United States Patent [19]
Holick

[11] Patent Number: 5,508,392
[45] Date of Patent: Apr. 16, 1996

[54] USE OF VITAMIN D GLYCOSIDES, VITAMIN D ORTHOESTER GLYCOSIDES, VITAMIN D ANALOG GLYCOSIDES AND VITAMIN D ANALOG ORTHOESTER GLYCOSIDES FOR THE TREATMENT OF OSTEOPOROSIS

[76] Inventor: Michael F. Holick, 31 Bishop La., Sudbury, Mass. 01776

[21] Appl. No.: 230,867

[22] Filed: Apr. 20, 1994

Related U.S. Application Data

[63] Continuation of Ser. No. 997,951, Dec. 29, 1992, abandoned.

[51] Int. Cl.$^6$ .......................... C07H 15/24; C07C 41/00; C07C 35/22
[52] U.S. Cl. .......................... 536/18.1; 536/4.1; 536/17.2; 536/53; 536/55.2; 568/665; 568/817; 568/819
[58] Field of Search .......................... 514/35, 167, 171; 568/665, 817, 819; 536/4.1, 18.1, 17.2, 55.2, 53

[56] References Cited

U.S. PATENT DOCUMENTS

| | | | |
|---|---|---|---|
| 4,410,515 | 10/1983 | Holick et al. | 424/180 |
| 4,740,364 | 4/1988 | Hodgen | 424/9 |
| 4,772,467 | 9/1988 | Pak | 424/127 |
| 4,894,373 | 1/1990 | Young | 514/239.2 |
| 5,013,728 | 5/1991 | Grodberg | 514/171 |
| 5,104,864 | 4/1992 | DeLuca et al. | 514/167 |
| 5,116,828 | 5/1992 | Miura et al. | 514/171 |
| 5,167,953 | 12/1992 | Holick et al. | 424/59 |
| 5,194,248 | 3/1993 | Holick | 424/59 |

FOREIGN PATENT DOCUMENTS 9105537 5/1991 WIPO.

OTHER PUBLICATIONS

Riggs, B. L. and Melton, L. J., "Involutional Osteoporosis," *N. Eng. J. Med.* 314:1676–1684 (1986).

Riggs, B. L. and Nelson, K. I., "Effect of Long Term Treatment with Calcitriol on Calcium Absorbtion and Mineral Metabolism in Postmenopausal Osteoporosis," *J. Clin. Endocrinol. Metab.* 61:457–461 (1985).

Chemical Abstracts, vol. 83, No. 18, abstract 152290w, 1975.

Chemical Abstracts, vol. 84, No. 5, abstract 31373m, 1976.

Napoli et al., "Solanum glaucophyllum As Source of 1,25–Dihydroxyvitamin $D_3$," *J. Biological Chemistry* 252(8):2580–2583 (1977).

Napoli et al, "Blood Calcium Regulators," Burger's Medicinal Chemistry, 4th Ed., Part II, pp. 725–739 (1979).

Caniggia, A. et al., "Long–Term Treatment with Calcitriol in Postmenopausal Osteoporosis," *Metabolism* 39 Suppl. 1:43–49 (Apr. 1990).

Kragballe, K., "Treatment of Psoriassis by the Topical Application of the Novel Cholecalciferol Analogue Calcipotriol (MC 903)," *Arch. Dermatol.* 125:1647–1652 (Dec. 1989).

Tilyard, M. W. et al., "Treatment of Postmenopausal Osteoporosis with Calcitriol or Calcium," *New England Journal of Medicine* 326(6):357–362 (Feb. 6, 1992).

*Primary Examiner*—Ronald W. Griffin
*Attorney, Agent, or Firm*—Sterne, Kessler, Goldstein & Fox

[57] ABSTRACT

The present invention relates to methods for the treatment of prevention of osteoporosis by the administration of a vitamin D glycoside or vitamin D orthoester glycoside, or an analog thereof.

6 Claims, No Drawings

USE OF VITAMIN D GLYCOSIDES, VITAMIN D ORTHOESTER GLYCOSIDES, VITAMIN D ANALOG GLYCOSIDES AND VITAMIN D ANALOG ORTHOESTER GLYCOSIDES FOR THE TREATMENT OF OSTEOPOROSIS

This application is a continuation, of application Ser. No. 07/997,951, filed Dec. 29, 1992, now abandoned.

FIELD OF THE INVENTION

The invention is in the field of Medical Chemistry.

BACKGROUND OF THE INVENTION

It is well known that females at the time of menopause suffer a marked loss of bone mass giving rise ultimately to osteopenia, which in turn gives rise to spontaneous crush fractures of the vertebrae and fractures of the long bones. This disease is generally known as postmenopausal osteoporosis and presents a major medical problem, both in the United States and most other countries where the life-span of females reaches ages of at least 60 and 70 years. Generally the disease, which is often accompanied by bone pain and decreased physical activity, is diagnosed by one or two vertebral crush fractures with X-ray evidence of diminished bone mass. It is known that this disease is accompanied by diminished ability to absorb calcium, decreased levels of sex hormones, especially estrogen and androgens, and a negative calcium balance.

Methods for treating the disease have varied considerably but to date no really satisfactory treatment is yet known. For example, calcium supplementation by itself has not been successful in preventing or curing the disease and the use of sex hormones, especially estrogen, which has been reported to be effective in preventing the rapid loss of bone mass experienced in postmenopausal women, has been complicated by the tear of its possible carcinogenicity. Other treatments, for which variable results have again been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large amounts of fluoride administered.

U.S. Pat. No. 4,725,596 discloses methods for treating or preventing metabolic bone disease characterized by the loss of bone mass by administering at least one compound having the formulae (I) and (II):

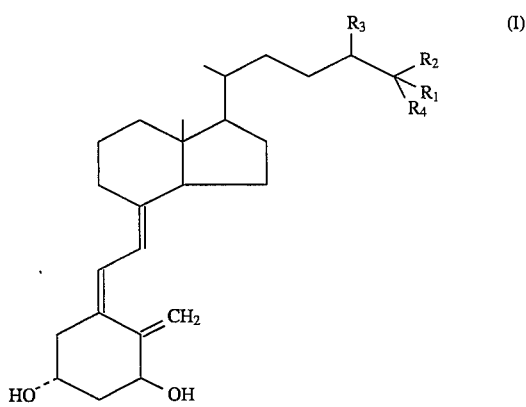

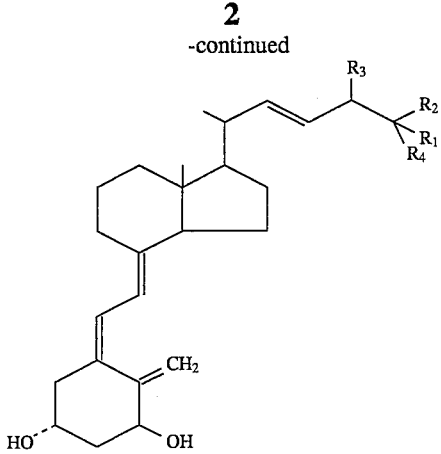

where $R_1$, $R_2$ and $R_3$ are each selected from the group consisting of hydrogen, hydroxyl, lower alkyl, acyl and O-alkyl and $R_3$ is selected from the group consisting of hydrogen, hydroxyl, keto, lower alkyl, acyl and O-alkyl.

See also, Tilyard, M. W. et al., *N. Eng. J. Med.* 326:357–362 (1992) and Caniggia. A., et al., *Metabolism* 39:43–49 (1990), who disclose the treatment of osteoporosis with calcitriol (1α,25-dihydroxyvitamin $D_3$). However, this method has the significant disadvantage that high levels of these compounds, e.g., 1α,25-dihydroxyvitamin $D_3$, causes an increase of the blood calcium level above the normal range and concomitant toxicity.

U.S. Pat. No. 4,410,515 discloses the following compounds having Formula (III) which are active in maintaining calcium and phosphorus metabolism and are useful for treating hypocalcemia in animals:

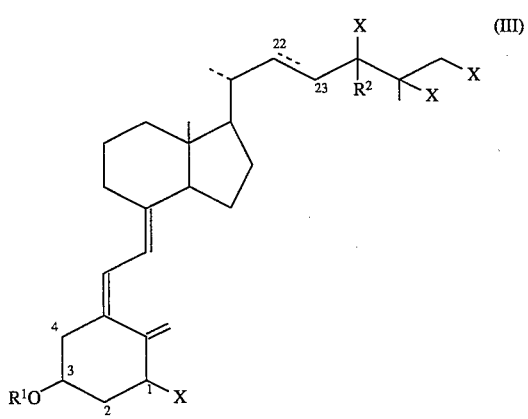

wherein the double bond between positions C-22 and C-23 is single or double; $R^2$ is hydrogen, $CH_3$ or $CH_2CH_3$; X is selected from the group consisting of hydrogen and $-OR^1$, where $R^1$ is hydrogen or a straight or branched chain glycosidic residue containing 1–20 glycosidic units per residue; with the proviso that at least one of the $R^1$ is glycosidic residue.

SUMMARY OF THE INVENTION

The present invention relates to a method for treating or preventing osteoporosis in an animal having osteoporosis or susceptible to osteoporosis, comprising administering to the animal an effective amount of a compound having the formula:

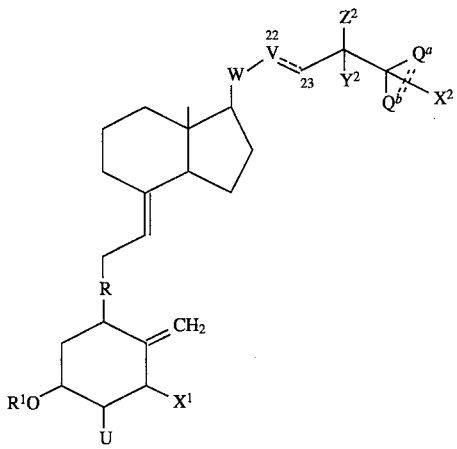

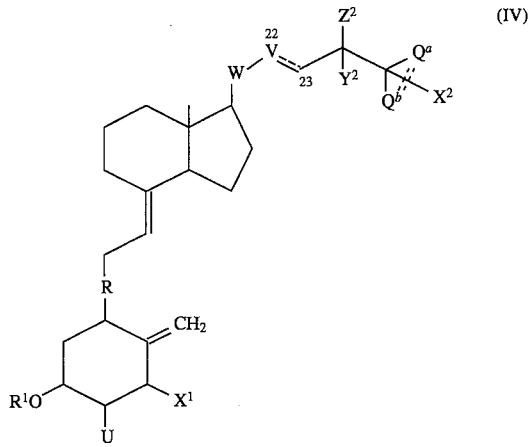

wherein the bond between C-22 and C-23 is a single or a double bond;

$Y^2$ is hydrogen, fluorine, methyl, ethyl or $OR^1$;

$Z^2$ is F, H or $X^2$;

U is hydrogen, —OH or —O—($C_2$-$C_4$ alkyl)—OH;

$Q^a$ is $CF_3$ or $CH_2X^2$;

$Q^b$ is $CF_3$ or $CH_3$;

R is a double bond or an epoxy group;

$X^1$ and $X^2$ are selected from the group consisting of hydrogen and $OR^1$;

$R^1$ is hydrogen or a straight or branched chain glycosidic residue containing 1–20 glycosidic units per residue, or $R^1$ is an orthoester glycoside moiety of the formula:

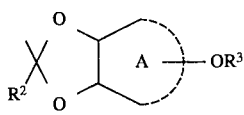

wherein A represents a glycofuranosyl or glycopyranosyl ring;

$R^2$ is hydrogen, lower alkyl ($C_1$-$C_4$), aralkyl ($C_7$-$C_{10}$), or aryl, with the proviso that aryl is phenyl or phenyl substituted by chloro, fluoro, bromo, iodo, lower $C_1$-$C_4$ alkyl, $C_1$-$C_4$ alkoxy; or naphthyl;

$R^3$ is hydrogen or a straight or branched chain glycosidic residue containing 1–20 glycosidic units per residue;

W is CH—$CH_3$ or O; and

V is $CH_2$ or O;

with the proviso that both W and V are not both O; and

"=====" is either a single bond between $Q^a$ and $Q_b$ or a hydrogen atom on $Q^a$ and $Q^b$, with the proviso that wherein "=====" is a single bond, then $X^2$ is H: and with the further proviso that at least one of the $R^1$ is either a glycosidic residue or an orthoester glycoside moiety.

DESCRIPTION OF THE PREFERRED EMBODIMENTS

The invention is related to the discovery that compounds having Formula (IV) are useful in treating and preventing osteoporosis:

wherein the bond between C-22 and C-23 is a single or double bond;

$Y^2$ is hydrogen, fluorine, methyl, ethyl or $OR^1$;

$Z^2$ is F, H or $X^2$;

U is hydrogen, —OH or —O—($C_2$-$C_4$ alkyl)—OH;

$Q^a$ is $CF_3$ or $CH_2X^2$;

$Q^b$ is $CF_3$ or $CH_3$;

R is a double bond or an epoxy group;

$X^1$ and $X^2$ are selected from the group consisting of hydrogen, and $OR^1$, $R^1$ is hydrogen or a straight or branched chain glycosidic residue containing 1–20 glycosidic units per residue, or $R^1$ is an orthoester glycoside moiety of the Formula (V):

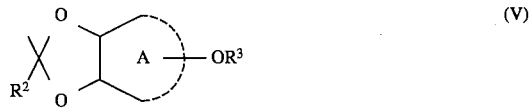

wherein A represents a glycofuranosyl or glycopyranosyl ring;

$R^2$ is hydrogen, lower alkyl, aralkyl, or aryl, with the proviso that aryl is phenyl or phenyl substituted by chloro, fluoro, bromo, iodo, lower $C_1$-$C_4$ alkyl, $C_1$-$C_4$ alkoxy; or naphthyl; and $R^3$ is hydrogen or a straight or branched chain glycosidic residue containing 1–20 glycosidic units per residue, with the proviso that at least one of the $R^1$ is either a glycosidic residue or an orthoester glycoside moiety;

W is CH—$CH_3$ or O; and

V is $CH_2$ or O;

with the proviso that both W and V are not both O; and

"=====" is either a single bond between $Q^a$ and $Q^b$ or a hydrogen atom on $Q^a$ and $Q^b$, with the proviso that wherein "=====" is a single bond, then $X^2$ is H.

Any animal which experiences osteoporosis and which may benefit from the vitamin D glycosides and orthoester glycosides of Formula IV may be treated according to the present invention. Preferred animals are of course humans, in particular, pre- or post menopausal women. When administered to a pre-menopausal woman, it is possible to prevent osteoporosis. When administered to a post-menopausal woman, it is possible to reverse the adverse consequences of osteoporosis mentioned above, and arrest the further deterioration of the bones.

The vitamin D glycosides and orthoester glycosides of the present invention have the distinct advantage that they promote calcium absorption through the intestine without effecting calcium mobilization from the bones. Thus, unlike 1,25-dihydroxyvitamin $D_3$ which effects calcium mobilization from the bones, the vitamin D glycosides and orthoester glycosides of Formula IV are uniquely suited for the treatment of osteoporosis.

By glycosidic units are meant glycopyranosyl or glycofuranosyl, as well as their amino sugar derivatives. The residues may be homopolymers, random or alternating or block copolymers thereof. The glycosidic units have free hydroxy groups, or hydroxy groups acylated with a group $R^4$—(C=O)—, wherein $R^4$ is hydrogen, lower $C_{1-6}$ alkyl, $C_{6-10}$ substituted or unsubstituted aryl or $C_{7-16}$ aralkyl. Preferably, $R^4$ is acetyl or propionyl; phenyl, nitrophenyl, halophenyl, lower alkyl substituted phenyl, lower alkoxy substituted phenyl, and the like or benzyl, lower alkoxy substituted benzyl and the like.

When the compounds of Formula (IV) have a double bond at position C-22 and a methyl group at C-24, they are derivatives of vitamin $D_2$, whereas if the bond at that position is single, and there is a lack of $C_{24}$ alkyl, they are derivatives of vitamin $D_3$.

The compounds useful in the practice of the invention contain at least one glycoside residue at positions 1, 3, 24, 25 or 26. They may contain, however, more than one and up to five glycoside residues simultaneously.

Preferred are those glycosides derived from vitamins $D_3$ or $D_2$; 1-hydroxyvitamins $D_3$ or $D_2$; 1,24-dihydroxyvitamins $D_2$ and $D_3$; 1,25-dihydroxyvitamins $D_3$ and $D_2$; 24,25-dihydroxyvitamins $D_3$ or $D_2$; 25,26-hydroxyvitamins $D_3$ or $D_2$; 1,24,25-trihydroxyvitamins $D_3$ or $D_2$; and 1,25,26-trihydroxyvitamins $D_3$ or $D_2$. Among the most preferred are the glycosides of 1-hydroxyvitamins $D_3$ or $D_2$; and 1,25-dihydroxyvitamins $D_3$ or $D_2$, 1,24-dihydroxyvitamin $D_3$, 5,6-epoxy derivatives of vitamin D and its metabolites, 2-β-(3-hydroxypropoxy)-1 alpha,25-dihydroxyvitamin $D_3$, as well as the side chain fluoro derivatives of 1,25-$(OH)_2$ vitamin D and 1-(OH) vitamin D. Also preferred are 20- and 22-oxa vitamin D derivatives including 20-oxa-1α(OH)D, 20-oxa-1α,25$(OH)_2D_3$, 22-oxa-1α(OH)$D_3$ and 22-oxa-1α, 25(OH)$D_3$ as well as pseudo-1-alpha-hydroxyvitamin D derivatives such as dihydrotachysterol and 5,6-trans vitamin $D_3$ and their 25-hydroxy derivatives. Also preferred is calcipotriol having the formula:

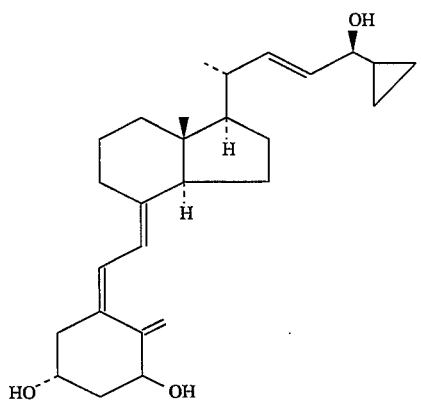

See Krayballe, K., *Arch. Dertnatol.* 125:1647 (1989).

The most preferred glycosides include vitamin $D_3$, 3β-(β-D-glucopyranoside); vitamin $D_3$, 3β-(β-D-fructofuranoside); vitamin $D_3$, 3β-(galactosyl); vitamin $D_3$, 3β-(β-maltoside); vitamin $D_3$, 3β-(β-lactoside); vitamin $D_3$, 3β-(β-trehaloside); vitamin $D_3$, 3β-raffinoside; vitamin $D_3$, 3β-gentiobioside; 1α-hydroxyvitamin $D_3$, 3β-(β-D-glucopyranoside); 1α-hydroxyvitamin $D_3$, 3β-(β-D-fructofuranoside); 1α-hydroxyvitamin $D_3$, 3β-(β-cellobioside); 1α-hydroxy-3β-(β-maltosyl)vitamin $D_3$; 1α-hydroxy-3β-raffinosylvitamin $D_3$; 1α-hydroxy-3β-gentiobiosylvitamin $D_3$; 1α-(β-D-glucopyranosyl)vitamin $D_3$; 1α-(β-D-fructofuranosyl)vitamin $D_3$; 1α-(β-galactosyl)vitamin $D_3$; 1α-(β-maltosyl)-vitamin $D_3$; 1α-(β-lactosyl)vitamin $D_3$; 1α-(β-trehalosyl)vitamin $D_3$; 1α-raffinosylvitamin $D_3$; 1α-gentiobiosylvitamin $D_3$; 1α, 25-dihydroxyvitamin $D_3$, 3β-(β-D-fructofuranoside); 1α, 25-dihydroxyvitamin $D_3$,3β-(β-D-glucopyranoside ); 1α-(β-D-glycopyranosyl)-25-hydroxyvitamin $D_3$; 1α-(β-D-fructofuranosyl)-25-hydroxyvitamin $D_3$; 1α-hydroxy-25(β-D-fructofuranosyl)-vitamin $D_3$; 1α-hydroxy, 25-(β-glucopyranosyl)vitamin $D_3$; 1α-hydroxy, 25-(β-maltosyl)vitamin $D_3$; 1α-hydroxy, 25-(β-lactosyl)vitamin $D_3$; 1α-hydroxy, 25-β-trehalosylvitamin $D_3$; 1α-hydroxy, 25-raffinosylvitamin $D_3$; and 1α-hydroxy, 25-gentiobiosylvitamin $D_3$. Also included are 1α,24-dihydroxyvitamin $D_3$, 3β-(β-D-glucopyranoside); 1α,24-dihydroxyvitamin $D_3$, 3β-(β-D-fructofuranoside); 1α-(β-D-glycopyranosyl)-24-hydroxyvitamin $D_3$; 1α-(β-D-fructofuranosyl)-24-hydroxyvitamin $D_3$; 1α-hydroxy-24(β-D-fructofuranosyl) vitamin $D_3$; 1α-hydroxy-24-(β-glycopryanosyl)vitamin $D_3$; 1α-hydroxy, 24-(β-maltosyl)vitamin $D_3$; 1α-hydroxy, 24-(β-lactosyl)vitamin $D_3$; 1α-hydroxy, 24-β-trehalosylvitamin $D_3$; 1α-hydroxy, 24-raffinosylvitamin $D_3$; and 1α-hydroxy, 24-gentiobiosyivitamin $D_3$.

In the case of multihydroxylated forms of the vitamins (e.g.: 1,25-dihydroxyvitamin $D_3$ has three hydroxy groups, at positions 1, 3 and 25), the preferred compounds of the invention are those wherein less than all of the multiple hydroxy groups are glycosylated, most preferably those were only one of the multiple hydroxy groups is glycosylated.

The glycosides can comprise up to 20 glycosidic units. Preferred, however, are those having less than 10, most preferred, those having 3 or less than 3 glycosidic units. Specific examples are those containing 1 or 2 glycosidic units in the glycoside residue.

The glycopyranose or glycofuranose rings or amino derivatives thereof may be fully or partially acylated or completely deacylated. The completely or partially acylated glycosides are useful as defined intermediates for the synthesis of the deacylated materials.

Among the possible glycopyranosyl structures are glucose, mannose, galactose, gulose, allose, altrose, idose, or talose. Among the furanosyl structures, the preferred ones are those derived from fructose, arabinose or xylose. Among preferred diglycosides are sucrose, cellobiose, maltose, lactose, trehalose, gentiobiose, and melibiose. Among the triglycosides, the preferred ones may be raffinose or gentianose. Among the amino derivatives are N-acetyl-D-galactosamine, N-acetyl-D-glucosamine, N-acetyl-D-mannosamine, N-acetylneuraminic acid, D-glucosamine, lyxosylamine, D-galactosamine, and the like.

When more than one glycosidic unit is present on a single hydroxy group (i.e., di or polyglycosidic residues), the individual glycosidic rings may be bonded by 1-1, 1-2, 1-3, 1-4, 1-5 or 1-6 bonds, most preferably 1-2, 1-4 and 1-6. The linkages between individual glycosidic rings may be α or β.

The configuration of the oxygen linkage of a hydroxy group, or glycosidic residue attached to the vitamin $D_3$ or $D_2$ molecule may be either α (out of the plane of the paper) or β (into the plane of the paper). It is preferred if the configuration of the 3-hydroxy or glycosidoxy group at C-3 be β, and that, independently or simultaneously the configuration of the hydroxy or glycosidoxy at C-1 be α.

The starting vitamin D compounds are prepared or obtained according to methods which are well known to those of ordinary skill in the art. In particular, the 5,6-epoxy derivatives of vitamin $D_3$ are obtained as described in Jpn. Kokai Tokkyo Koho JP 58,216,178 [83,216,178], Dec. 15, 1983. The fluoro derivatives are made or obtained as described in Shiina, et al., *Arch. Biochem. Biophys.* 220:90 (1983). Methods for preparing the 20- and 22-oxa vitamin D derivatives are disclosed by Abe, J., et al., *Vitamin D Molecular, Cellular and Clinical Endocrinology*, p. 310–319, Walter de Gruyter & Co., Berlin (1988). U.S. Pat. No. 4,719,205 to DeLuca et al. discloses methods for the preparation of 22,23-cis-unsaturated, 1-hydroxyvitamin D compounds. U.S. Pat. No. 4,634,692 to Partridge et al. discloses methods for the preparation of 1,25-dihydroxy-24 (R or S)-fluorovitamin D. Japanese Patent Application, publication no. J55 111–460, discloses methods for the preparation of 24,24-difluoro-25-hydroxyvitamin $D_3$.

The water soluble glycosidic derivatives of the aforementioned compounds may be obtained according to Holick, U.S. Pat. No. 4,410,515, the contents of which are fully incorporated by reference herein. The vitamin D glycosyl orthoester compounds may be obtained according to U.S. Pat. No. 4,521,410, the contents of which are fully incorporated by reference herein.

The compounds of the invention can be administered in any appropriate pharmaceutically acceptable carrier for oral, parenteral, or topical administration. They can be administered by any means that treats or prevents osteoporosis in animals, especially humans. The dosage administered will be dependent upon the age, health and weight of the recipient, kind of concurrent treatment, if any, frequency of treatment and the nature of the effect desired. For example, systemic daily dosage of $1\alpha$-($\beta$-glucopyranosyl )-25-hydroxyvitamin $D_3$ will be from about 0.001 micrograms/kg to 100 micrograms/kg preferably 0.01 to 1.0 micrograms per kg of body weight. Normally, from about 0.1 to 100 micrograms/kg per day of the glycoside or orthoester glycoside, in one or more dosages per day is effective to obtain the desired results. One of ordinary skill in the art can determine the optimal dosages and concentrations of other active vitamin D glycoside and orthoester glycoside compounds with only routine experimentation.

The compounds can be employed in dosage forms such as tablets, capsules, powder packets, or liquid solutions, suspensions or elixirs for oral administration, sterile liquid for formulations such as solutions or suspensions for parenteral use. Alternatively, the compounds may be administered transdermally via a patch or ointment and the like. The active ingredient will ordinarily be present in an amount of at least $10^{-6}$% by weight based upon the total weight of the composition, and not more than 90% by weight. An inert pharmaceutically acceptable carrier is preferably used. Among such carriers include 95% ethanol, vegetable oils, propylene glycols, saline buffers, etc.

Having now generally described this invention, the same will be understood by reference to the following examples which are provided herein for purposes of illustration only and are not intended to be limiting unless otherwise specified.

Example 1

Biologic Activity of 1,25-Dihydroxyvitamin $D_3$-$3\beta$-glucoside in Male Rats A study in male rates was conducted to evaluate the potential biologic activity of $1\alpha$-($3\beta$-glucopyranosyl),25-dihydroxyvitamin $D_3$ (1,25$(OH)_2D_3$-$3\beta$-glucoside). Male rats from Charles River were placed on rat chow for three days. They received by oral administration in 0.1 ml of propylene glycol one of the following compounds: 1,25$(OH)_2D_3$ (0.625 $\eta$mol), 1,25$(OH)_2D_3$ (6.25 $\eta$mol), 1,25$(OH)_2D_3$-$3\beta$-glucoside (6.25 $\eta$mol). A control group received 0.1 ml of propylene glycol. The animals were dosed for five days. Twenty-four hour urine collections were made on Day 4 of the experiment, and on the fifth day, blood was collected for determination of serum calcium and 1,25$(OH)_2D_3$ concentrations. As can be seen in Table 1, 1,25$(OH)_2D_3$ increased the urinary calcium excretion and increased serum concentrations of calcium above the control values. 6.25 $\eta$mol of 1,25$(OH)_2D_3$-$3\beta$-glucoside also increased the excretion of calcium in the urine but did not have a significant effect on the serum calcium concentration. Determination of serum concentrations of 1,25$(OH)_2D_3$ revealed that elevated levels of 1,25$(OH)_2D_3$ occurred in rats receiving 1,25$(OH)_2D_3$ at both doses as well as rats that received the 1,25$(OH)_2D_3$-$3\beta$-glucoside.

The increase in the excretion of urinary calcium is an indicator that both 1,25$(OH)_2D_3$ and 1,25$(OH)_2D_3$-$3\beta$-glucoside increase the efficiency of intestinal calcium absorption and mobilization of calcium from the bone. However, at the low and high dose of 1,25$(OH)_2D_3$, the undesirable effect on increasing the blood calcium above the normal range was observed. On the other hand, animals that received the highest dose of 1,25$(OH)_2D_3$-$3\beta$-glucoside did not show an increase in the blood calcium above the normal range.

In osteoporosis, the blood calcium levels are normal. In order to effectively treat osteoporosis, it is necessary to provide 1,25$(OH)_2D_3$ to stimulate the anabolic activity of bone cells. However, as shown above, 1,25$(OH)_2D_3$ causes an undesired increase in blood calcium levels. Therefore, the vitamin D glycosides and orthoester glycosides are uniquely effective for the treatment of osteoporosis by increasing in a physiologic manner the efficiency of intestinal calcium absorption and bone calcium mobilization and increasing circulating concentrations of 1,25$(OH)_2D_3$, without the side effects associated with the administration of 1,25$(OH)_2D_3$.

TABLE 1

Evaluation of $1,25(OH)_2D_3$ and $1,25(OH)_2D_3$-3β-Glucoside in Male Rats

| Compound | Dose (ηmoles) | 24 Hour Urine Ca (mg/24h day 4) | Serum Ca (mg % day 5) | Serum $1,25(OH)_2D_3$ (pg/ml) |
|---|---|---|---|---|
| Vehicle | 0 | 19 | 10.4 | 85 |
| $1,25(OH)_2D_3$ | 0.625 | 43 | 11.4 | 356 |
| $1,25(OH)_2D_3$ | 6.25 | 38 | 13 | 1409 |
| $1,25(OH)_2D_3$-glc | 6.25 | 40 | 10.6 | 358 |

From the foregoing description, one skilled in the art can easily ascertain the essential characteristics of this invention, and without departing from the spirit and scope thereof, can make various changes and modifications if the invention to adapt it to various usages and conditions without undue experimentation. All patents and publications cited herein are incorporated by reference in their entirety.

What is claimed is:

1. A method for treating or preventing osteoporosis in an individual having osteoporosis or susceptible to osteoporosis without causing the side effects associated with the administration of 1,25-dihydroxyvitamin $D_3$, comprising administering to said individual an effective amount of a compound having the formula:

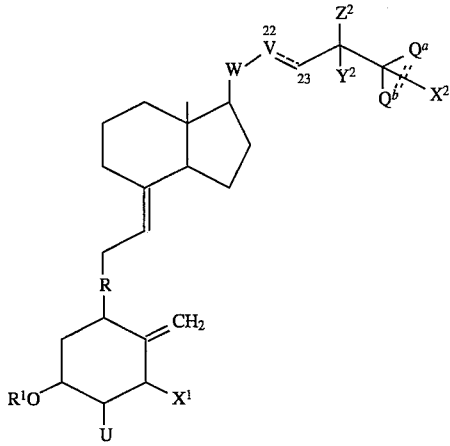

wherein the bond between C-22 and C-23 is a single bond or a double bond;

$Y^2$ is hydrogen, fluorine, methyl, ethyl or $OR^1$;

$Z^2$ is F, H or $X^2$;

U is hydrogen, —OH or —O—($C_2$–$C_4$ alkyl)—OH;

$Q^a$ is $CF_3$ or $CH_2X^2$;

$Q^b$ is $CF_3$ or $CH_3$;

R is a double bond or an epoxy group;

$X^1$ and $X^2$ are selected from the group consisting of hydrogen and $OR^1$;

$R^1$ is hydrogen or a straight or branched chain glycosidic residue containing 1–20 glycosidic units per residue, or $R^1$ is an orthoester glycoside moiety of the formula:

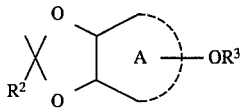

wherein A represents a glycothranosyl or glycopyranosyl ring;

$R^2$ is hydrogen, alkyl ($C_1$–$C_4$), aralkyl ($C_7$–$C_{10}$), or aryl, with the proviso that aryl is phenyl or phenyl substituted by chloro, fluoro, bromo, iodo, $C_1$–$C_4$ alkyl, $C_1$–$C_4$ alkoxy; or naphthyl;

$R^3$ is hydrogen or a straight or branched chain glycosidic residue containing 1–20 glycosidic units per residue;

W is CH—$CH_3$ or O: and

V is $CH_2$ or O;

with the proviso that both W and V are not both O; and

"=====" is either a single bond between $Q^a$ and $Q^b$ or a hydrogen atom on $Q^a$ and $Q^b$, with the proviso that wherein "=====" is a single bond, then $X^2$ is H; and with the further proviso that at least one of the $R^1$ groups is either a β-glycosidic residue or an orthoester β-glycoside moiety.

2. The method of claim 1, wherein said compound is $1,25(OH)_2D_3$-3β-glucoside.

3. The method of claim 1, wherein said compound is administered in an amount ranging from about 0.1 to 100 micrograms/kg per day.

4. The method of claim 1, wherein said compound is administered as part of a pharmaceutical composition comprising a pharmaceutically acceptable carrier.

5. The method of claim 1, wherein said individual is suffering from or has suffered from menopause.

6. The method of claim 1, wherein said compound is administered to a woman prior to the onset of menopause.

* * * * *

UNITED STATES PATENT AND TRADEMARK OFFICE
CERTIFICATE OF CORRECTION

PATENT NO. : 5,508,392

DATED : April 16, 1996

INVENTOR(S): Holick

It is certified that an error appears in the above-identified patent and that said Letters Patent is hereby corrected as shown below.

In column 10, at line 23, delete "glycothranosyl" and insert therein --glycofuranosyl--.

Signed and Sealed this

Nineteenth Day of November, 1996

*Attest:*

BRUCE LEHMAN

*Attesting Officer*   *Commissioner of Patents and Trademarks*